United States Patent [19]

Kater

[11] Patent Number: 5,046,509
[45] Date of Patent: Sep. 10, 1991

[54] DEVICE FOR THE CONDITIONING, HANDLING AND MEASUREMENT OF BLOOD

[75] Inventor: John A. R. Kater, Santa Ana, Calif.
[73] Assignee: SpaceLabs, Inc., Bothell, Wash.
[21] Appl. No.: 292,490
[22] Filed: Dec. 30, 1988
[51] Int. Cl.$^5$ .............................................. A61B 5/00
[52] U.S. Cl. .................................... 128/764; 604/272
[58] Field of Search ................ 128/673, 760, 763–766, 128/770; 604/51–53, 93, 187, 188, 264, 271, 280, 283, 284, 403

[56] References Cited

U.S. PATENT DOCUMENTS

| | | | |
|---|---|---|---|
| 3,920,002 | 11/1975 | Dye et al. | 128/760 |
| 4,140,108 | 2/1979 | Nugent | 128/760 |
| 4,215,690 | 8/1980 | Oreopoulos et al. | 609/272 |
| 4,385,637 | 5/1983 | Akhavi | 128/763 |
| 4,447,235 | 5/1984 | Clarke | 128/760 |
| 4,763,648 | 8/1988 | Wyatt | 128/673 |
| 4,838,855 | 6/1989 | Lynn | 128/764 |
| 4,844,087 | 7/1989 | Garg | 128/763 |

Primary Examiner—Max Hindenburg
Attorney, Agent, or Firm—Seed and Berry

[57] ABSTRACT

An improved blood sampling device is disclosed which includes a coupling device connected to a needle for receiving blood withdrawn from a patient. The coupling device includes first and second ports in flow communication with the needle and is adapted to conduct blood to either the first or second port. The first port includes an adapter sleeve which is adapted to receive a vacutainer-type blood storage device for storing blood samples taken from the patient. A microporous hydrophobic plug is positioned within the coupling device intermediate the first port and the needle for venting air which is trapped within the coupling device during the initial stages of the sampling operation. The second port is connected to the coupling device intermediate the plug and the needle and is adapted to receive a syringe for temporarily storing a first portion of blood withdrawn from the patient thereby to ensure that blood subsequently delivered to the vacutainer contains gases having relative partial pressures and activities of ionic species substantially equal to those of the patient's in vivo conditions.

35 Claims, 1 Drawing Sheet

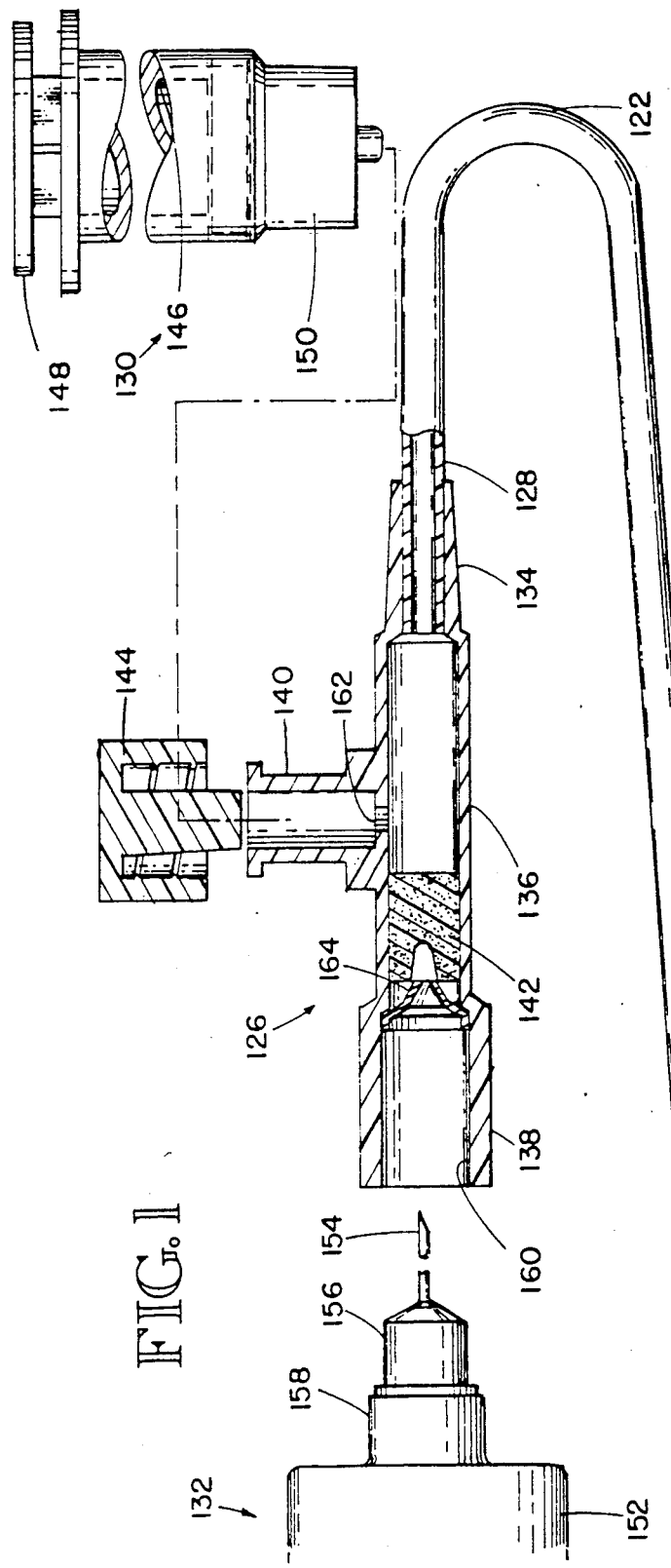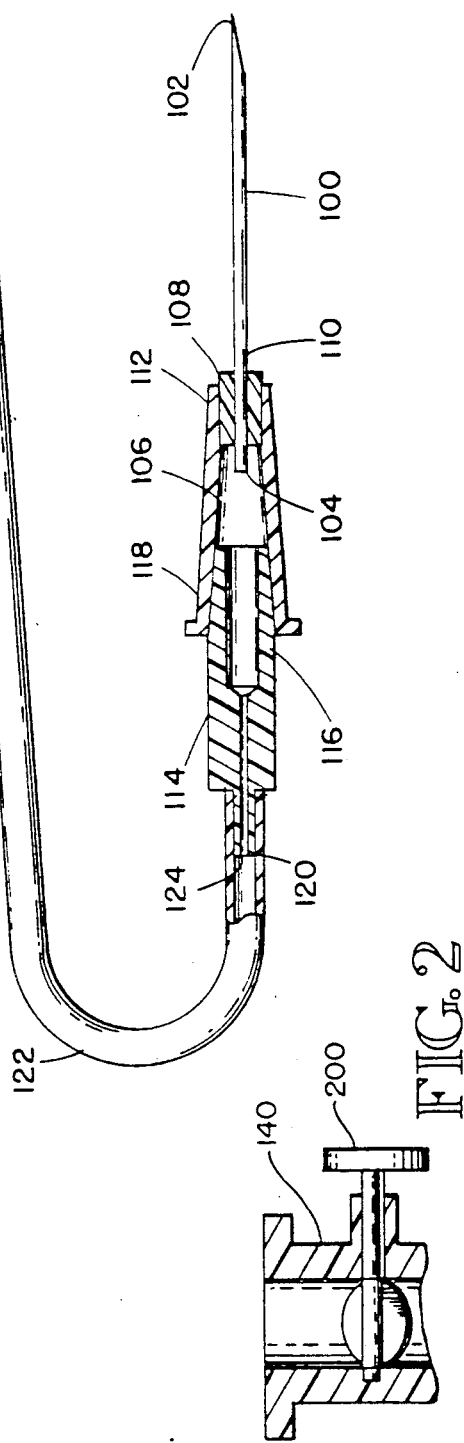

DEVICE FOR THE CONDITIONING, HANDLING AND MEASUREMENT OF BLOOD

TECHNICAL FIELD

The present invention is directed toward apparatus for removing blood samples from a patient, and, more particularly, toward an improved blood sampling device which allows blood samples to be taken a manner so that the partial pressure of gases in the sample is substantially equal to the partial pressure of gases within the patient's in vivo blood.

BACKGROUND OF THE INVENTION

Within the medical field, there is a need to determine the in vivo conditions of gas equilibrium within the blood of a patient. Medical personnel will typically be concerned with the partial pressures of oxygen, and carbon dioxide. They are also concerned with those ionic species whose activities are related to blood gas equilibria, such as, the activities of hydrogen and calcium ions.

For a blood sample to be valid for blood gas analysis, the sample must be collected under anaerobic conditions, i.e., collected so that the blood is not exposed to gases outside of the patient's body, to thereby avoid a shift in the partial pressures of the gases to be examined. Current and commercially available arterial blood sampling devices are not generally adequate for ensuring the integrity of anaerobic blood sampling. As an example of a prior art device, a syringe and a vented plunger is used to slowly withdraw blood from the patient into the barrel of the syringe by pulling the vented plunger away from a zero airspace within the barrel until the correct volume of blood is obtained from the patient. These devices, however, still allow for a certain degree of exposure of the blood sample to outside air. A certain amount of outside air will be contained within the barrel prior to any movement of the plunger. Accordingly, the initial portion of blood will be exposed to this air thereby altering the partial pressures of gases contained in this initial sample. Since no means are provided for discarding the initial portion of blood withdrawn, the entire sample will be contaminated.

Furthermore, using the above-described device, no provision is made for protecting the medical operator of the device against accidental puncture or exposure to contaminated blood during the procedure.

Other devices, such as the Becton and Dickenson (BD) Vacutainer and Vacutainer Adapter display improved performance in protecting the medical operator from exposure to withdrawn blood. These devices too, however, allow a certain amount of exposure of the initial portions of the blood sample to outside air, thereby contaminating the entire sample.

In addition to the foregoing inadequacies of the prior art, no blood sampling device is presently known which provides means for flushing or infusion of fluid, e.g., nutrients, drugs, etc., into the bloodstream while also allowing removal of an anaerobic blood sample.

Accordingly, it is desirable to provide apparatus for extracting an anaerobic blood sample from a patient. It is further desirable to provide apparatus for extracting a blood sample which also allows fluids to be infused into the bloodstream of the patient. It is further desirable to provide such a device which will allow for taking repeated samples without the need to make additional punctures or needle placements. It is also desirable to provide a device for extracting blood samples, which device may be left on the patient for scheduled interval sampling, or other subsequent sampling.

SUMMARY OF THE INVENTION

It is therefore an object of the present invention to provide a blood sampling device for extracting an anaerobic blood sample from a patient.

It is also an object of the subject invention to provide a blood sampling device adapted for extracting an initial, contaminated portion of the blood sample thereby to maintain the anaerobic integrity of the remainder of the sample.

It is a further object of the invention to provide a blood sampling device which will allow for infusion of external fluids into the bloodstream of the patient.

It is a still further object of the invention to provide a blood sampling device which will allow for repeated sampling without the need for additional punctures or needle placements.

It is yet another object of the present invention to provide a blood sampling device which may be left on the patient for scheduled interval sampling or other subsequent blood sampling.

These and other objects of the present invention are met by providing a coupling for use by medical personnel when extracting and storing blood from a patient. The coupling is particularly adapted for use with a needle assembly, wherein the needle is injected into the patient for withdrawing the blood sample. The coupling includes an elongated hollow shaft and a connector member attached to a first end of the shaft for fixedly coupling the needle assembly to the shaft thereby to allow blood withdrawn by the needle to be delivered to the shaft. The coupling further includes an adapter sleeve attached to a second end of the shaft for interfacing the shaft with various blood storage devices. A port is coupled to the shaft intermediate the adapter sleeve and the connector member and in flow communication with the connector member so that blood received by the shaft is in flow communication with the port.

In an alternative embodiment of the invention, apparatus is provided for venting air which is trapped in the shaft while blocking the flow of blood. More particularly, a flow control device, e.g., a microporous hydrophobic plug, is positioned within the shaft intermediate the port and the adapter sleeve for restricting the flow of blood from the shaft to the adapter sleeve while allowing the flow of air from the shaft to the adapter sleeve. In other alternative embodiments of the invention, a valve is provided intermediate the shaft and the port for allowing selective fluid communication between the shaft and the port.

Other alternative embodiments of the invention are particularly pointed out and distinctly claimed in the numbered paragraphs appended hereto. The invention, however, both as to organization and method of practice, may best be understood from a reading of the following detailed description, taken in conjunction with the figures.

BRIEF DESCRIPTION OF THE DRAWINGS

FIG. 1 is a cross-sectional illustration of the improved blood sampling device which is the subject of the present invention.

FIG. 2 is a cross-sectional illustration of an alternative embodiment for the sampling device illustrated in FIG. 1.

DETAILED DESCRIPTION OF THE INVENTION

With reference to FIG. 1, there is provided a cross-sectional diagram illustrating the improved blood sampling device that is the subject of the present invention. The blood sampling device comprises an elongated needle 100 having an insertion end 102 that is adapted to be inserted within the blood stream (arterial or venous) of a patient. The needle 100 further includes a mounting end 104 which is mounted to a first connector member 106 via a cylindrical seal 108. As is known in the art, the needle 100 includes a coaxial channel extending from the insertion end 102 to the mounted end 104 for conducting blood withdrawn from the patient to the first connector member 106.

The cylindrical seal 108 includes a central aperture 110 within which the mounting end 104 of the needle 100 is fixedly attached Furthermore, the cylindrical seal 108 is fixedly attached to a needle receiving end 112 of the first connector member 106. A second connector member 114 includes a mating end 116 adapted to mate with a mating end 118 of the first connector member 106 so that blood received by the first connector member from the needle 100 is conducted to the second connector member 114 via the mating connection 116, 118.

A first end 120 of a tubing 122 is sealably mounted to a mounting end 124 of the second connector member 114. The tubing 122 is provided for transporting blood withdrawn from the patient via the needle 100 to a coupling 126. Preferably, the tubing 122 is flexible so that the needle may be readily inserted within the blood stream of the patient and further such that after insertion, the medical personnel may manipulate the coupling 126 without causing unnecessary motion to the needle 100 and resulting discomfort to the patient. Further, the tubing 122 is preferably clear so that the medical operator can visibly observe blood being withdrawn from the patient.

The combination of the needle 100, the first connector member 106, the second connector member 114, and the tubing 122, comprises a needle assembly and may be readily constructed from needles, connectors and tubing known in the art. As an example, first and second connecter members 106 and 114 may comprise male and female Luer connectors, respectively, as is known in the art.

The coupling 126 is provided for interfacing a second end 128 of the tubing with first and second blood storage devices 130 and 132, respectively. To this end, the coupling 126 includes a connector member 134 having a central aperture for receiving the second end 128 of the tubing 122. The connector member 134 is integrally coupled to an elongated hollow shaft 136 so that blood delivered to the coupling 126 by the tubing 122 may be received within the interior of the shaft 136. An adapter sleeve 138 is integrally coupled to the shaft 136 at an end opposite that of the connector member 134. The adapter sleeve 138 is in liquid flow communication with the shaft 136 and is provided for receiving the second blood storage device 132 as will be described more fully hereinbelow.

The coupling 126 further includes a port 140 integrally coupled to the shaft 136 intermediate the adapter sleeve 138 and the connector member 134. The port 140 is provided for coupling the first blood storage device 130 to the shaft 136 of the coupling 126. A passageway 162 is provided in the shaft 136, proximate the port 140, so that the port 140 is in liquid flow communication with the connector member 134. Accordingly, blood delivered to the coupling 126 by the tubing 122 may be transported to the first and second blood storage devices 130 and 132, via the adapter sleeve 138 and port 140, for storage.

The coupling 126 also includes a plug 142 positioned within the shaft 136 intermediate the adapter sleeve 138 and the port 140. The plug 142 comprises a liquid flow control device such as, for example, a porous plug, for venting air trapped within the connector members 106, 114, tubing 122, shaft 136, and port 140 during the initial stages of the blood sampling operation. Accordingly, the plug 142 is adapted to allow the flow of air from the shaft 136 to the adapter sleeve 138 while restricting the flow of blood from the shaft to the adapter sleeve. In the presently preferred embodiment of the invention, the plug 142 comprises a microporous hydrophobic plug as is known in the art. It will be apparent to those skilled in the art, however, that other liquid flow control devices could be used instead of the presently preferred microporous hydrophobic plug 142.

As mentioned hereinabove, the port 140 is adapted for receiving a first blood storage device 130. A cap 144 is matably engageable with the port 140 to seal the port from inadvertent blood loss at times when the first blood storage device 130 is not connected to the coupling 126. In normal operation, however, the cap 144 will be removed from the port 140 and the first blood storage device 130 coupled thereto.

In the presently preferred embodiment of the invention, the first blood storage device 130 comprises a syringe of the type including a blood storage chamber 146 and a plunger 148 positioned within the blood storage chamber 146. As is known, in operation, the plunger 148 is slowly withdrawn from the blood storage chamber 146 so that blood may be drawn into the chamber. The blood storage device 130 further comprises a connector member 150 for coupling the blood storage device 130 to the port 140. In the presently preferred embodiment of the invention, the port 140 and the connector member 150 comprise male and female Luer connectors, respectively. However, it will be apparent to those skilled in the art that other connector members may be provided for sealably connecting the first blood storage device 130 with the coupling 126.

As an example, the port 140 may include a value 200 as illustrated in FIG. 2, for selectively allowing fluid communication between the shaft 136 and the first blood storage device 130. Appropriate devices for use as the valve 200 may be readily selected from several commercial embodiments of valves readily available to those skilled in the art. Other alternative apparatus may be substituted for the valve 200 to allow selective fluid communication between the shaft 136 and the port 140.

In operation, the cap 144 is removed from the port 140 and the blood storage device 130 coupled thereto. The needle 100 is then inserted within the blood stream of the patient so that blood may be withdrawn, or preferably allowed to flow freely under the patient's cardiac pressure, and delivered to the shaft 136 via the connectors 106, 114 and tubing 122. Air which is trapped within the connectors 106, 114, tubing 122, shaft 136 and port 140 is displaced and vented via porous plug 142 by the patient's blood entering the fluid path, as described above. Since the first portion of blood which is withdrawn or flows under cardiac pressure from the patient is exposed to the trapped air before it is vented, this blood may be substantially contaminated and therefore not appropriate for anaerobic blood sampling. Accordingly, this first portion of blood is withdrawn from the coupling 126 into the blood storage device 130 to be temporarily stored while an anaerobic blood sample is taken via second blood storage device 132. After the anaerobic blood sample is taken, the blood temporarily stored within the blood storage device 130 may be discarded or returned to the patient via the tubing 122 and needle 100.

To withdraw the anaerobic blood sample, the second blood storage device 132 is coupled to the coupling 126 via the adapter sleeve 138. The second blood storage device 132 may comprise a Becton and Dickenson (BD) Vacutainer and Vacutainer Adapter known in the art. The blood storage device 132 includes a blood storage chamber 152 for receiving the anaerobic blood sample withdrawn from the patient. A needle 154 is sealably coupled to a needle hub 156 and the combination sealably coupled to the blood storage chamber 152 via an adaptive coupling 158 (commonly referred to as a Vacutainer Adapter). As is known in the art, the needle 154 includes a sealing which prevents it from being in flow communication with the blood storage chamber 152. Further, as is known in the art, the blood storage chamber 152 is evacuated so that it does not contain any air that may contaminate blood withdrawn from the patient. The adaptive coupling 158 includes means for removing the sealing from the needle 154 to place the needle 154 in flow communication with the blood storage chamber 152.

The adapter sleeve 138 includes an interior adapter chamber 160 which is of a diameter to snugly receive the needle hub 156. The length of the adapter sleeve 138 and the positioning of the plug 142 within the shaft 136 is selected so that when the blood storage device 132 is fully inserted in the adapter sleeve 138, the needle 154 will extend through the plug 142 and be positioned intermediate the passageway 162 and the second end 128 of the tubing 122. To ensure that the needle is inserted within the coupling 126 in a manner to be coaxial with the shaft 136, a needle guide 164 is positioned within the coupling 126 intermediate the adapter sleeve 138 and the plug 142. The needle guide 164 is provided for receiving the needle 154 during insertion of the blood storage device 132 into the coupling 126 and for positioning the needle prior to insertion of the needle into the plug 142 so that the needle will be coaxial with the shaft 136.

In operation, to collect an anaerobic blood sample, the blood storage device 130 is coupled to the coupling 126 via the port 140 as described above. The needle 100 is inserted within the blood stream of the patient and air trapped within the needle 100, connectors 106, 114, tubing 122 and coupling 126 is vented via the plug 142 as also described above. The needle 154 of the blood storage device 132 is then inserted into the coupling 126 through the plug 142 so that it is positioned beyond the passageway 162, proximate the tubing 122. It is desirable to insert the needle 154 into the coupling 126 prior to storing the contaminated portion of the blood sample within the blood storage device 130 so that any minute portions of contaminated air trapped within the needle 154 will be vented via plug 142 or removed from the coupling 126 prior to taking the anaerobic blood sample.

After the needle 154 is properly inserted within the coupling 126, a first portion of contaminated blood is withdrawn from the coupling 126 into the blood storage device 130 for temporary storage. At this time, the seal of the needle 154 is removed by the adaptive coupling 158, as is known in the art, so that the anaerobic blood sample may be conducted to the blood storage chamber 152. It is preferable that the needle 154 is positioned within the coupling 126 interior of the shaft 136 intermediate the passageway 162 and the tubing 122 and proximate the second end 128 of the tubing 122 so that substantially all of the blood conducted to the blood storage chamber 152 is that received from the tubing 122 and not the blood storage chamber 146 of the blood storage device 130. Positioning of the needle 154 in this manner further maintains the integrity of the anaerobic blood sample.

In an alternative embodiment of my invention, it may be desirable to provide a valve or other selective coupling device that will allow the contaminated blood samples stored within the blood storage device 130 to be substantially isolated from the shaft 136 during the period of operation when the anaerobic blood sample is being taken.

As is common in the medical community, caps and other sealing devices may be provided, in addition to cap 144, to be placed on the needle 100 and to seal the chamber 160 of the adapter sleeve 138.

While only several presently preferred embodiments of my novel blood sampling device have been described in detail herein, many modifications and variations will readily become apparent to those skilled in the art. It is my intention, by the claims appended hereto, to embody all such modifications and variations as fall within the true scope and spirit of my invention.

I claim:

1. A blood sampling device for use by medical personnel to withdraw and store a blood sample from a patient comprising:
   needle means adapted to be inserted in the patient to withdraw the blood sample; and
   coupling means for coupling said needle means to blood storage devices, said coupling means including first and second ports and being adapted to conduct blood from said needle means to said first and second ports, said second port being intermediate said needle means and said first port; and
   means for venting air trapped within said coupling means through said first port while blocking the flow of blood.

2. The blood sampling device as recited in claim 1 wherein said means for venting air comprises flow control means positioned within said coupling means intermediate said first and second ports for restricting the flow of blood from said needle means to said first port while allowing the flow of air from said needle means to said first port.

3. The blood sampling device as recited in claim 2 wherein said flow control means comprises a microporous hydrophobic plug.

4. The blood sampling device as recited in claim 3, further comprising needle guide means for guiding a needle associated with a blood storage device through said plug so that the needle is coaxial with said coupling means.

5. The blood sampling device as recited in claim 2, further comprising blood storage means for temporarily storing a portion of blood withdrawn from the patient, said blood storage means being sealably coupleable to said second port.

6. The blood sampling device as recited in claim 5 wherein said blood storage means comprises a syringe.

7. The blood sampling device as recited in claim 2, further comprising means for sealing said second port.

8. The blood sampling device as recited in claim 2, further comprising valve means positioned intermediate said needle means and said second port for allowing selective fluid communication between said needle means and said second port.

9. The blood sampling device as recited in claim 2 wherein said needle means comprises a needle for insertion into the patient and an elongate tubing for conducting blood from said needle to said coupling means, said tubing being substantially clear to allow the medical personnel to see the blood being conducted through said tubing.

10. The blood sampling device as recited in claim 1, further comprising capping means for sealing said second port.

11. A blood sampling device for use by medical personnel in removing and collecting a sample of blood from a patient comprising:
  needle means for extracting blood from the patient;
  coupling means for selectively coupling blood storage devices to said needle means, said coupling means being fixed to said needle means, said coupling means including a first port for receiving blood storage devices and a hollow shaft intermediate said first port and said needle means, said coupling means further including a second port for receiving blood storage devices, said second port being attached to said shaft intermediate said first port and said needle means; and
  flow control means positioned interior of said shaft intermediate said first and second ports for restricting the flow of blood from said shaft to said first port but allowing the flow of gases from said shaft to said first port.

12. The blood sampling device as recited in claim 11, further comprising blood storage means for temporarily storing a portion of blood, said blood storage means being adapted to be sealably coupled to said second port for receiving blood delivered to said shaft from said needle means.

13. The blood sampling device as recited in claim 12 wherein said blood storage means comprises a syringe including a blood storage chamber and a plunger positioned within said blood storage chamber, said syringe further including means for sealably coupling said blood storage chamber to said second port.

14. The blood sampling device as recited in claim 11 wherein said flow control means comprises a microporous hydrophobic plug.

15. The blood sampling device as recited in claim 14, further including blood storage means for storing a sample of blood, said blood storage means being sealably mountable to said first port and including a needle adapted for insertion through said plug to thereby conduct blood from said shaft to said blood storage means.

16. The blood sampling device as recited in claim 15, further comprising guide means positioned within said shaft intermediate said plug and said first port for guiding said needle of said blood storage means through said plug in a manner such that said needle is coaxial with said shaft.

17. The blood sampling device as recited in claim 11, further comprising guide means positioned within said shaft intermediate said flow control means and said first port for guiding a needle associated with a blood storage device through said flow control means in a manner such that the needle is coaxial with said shaft.

18. The blood sampling device as recited in claim 11, further comprising valve means for selectively allowing fluid communication between said shaft and said second port.

19. The blood sampling device as recited in claim 11 wherein said needle means includes a needle for insertion in the patient to withdraw the blood sample and an elongate tubing for conducting blood withdrawn from the patient to said coupling means, said tubing being flexible and being substantially clear so that blood conducted thereby is visible to the medical personnel.

20. The blood sampling device as recited in claim 19, further comprising a syringe including a blood storage chamber and a plunger positioned within said blood storage chamber, said syringe further including means for sealably coupling said blood storage chamber to said second port.

21. A blood sampling device for use by medical personnel for removing and collecting a blood sample from a patient comprising:
  a first elongate needle member having an insertion end and a mounting end, said insertion end being adapted to be inserted into the patient, said first needle member having a coaxial channel for transporting the blood withdrawn from the patient from said insertion end to said mounting end;
  a first female connector having a needle receiving end, a mating end and a coaxial channel extending from said needle receiving end to said mating end;
  means for fixedly and sealably coupling said mounting end of said first needle member to said needle receiving end of said first female connector so that blood withdrawn from the patient is transported to said first female connector by said first needle member;
  a first male connector having a mating end, a mounting end and a coaxial channel extending from said mating end to said mounting end, said mating end of said first male connector being sealably mated to said mating end of said first female connector so that blood transported to said first female connector will be received by said first male connector;
  an elongate tubing having first and second ends and a channel extending from said first end to said second end, said first end of said tubing being sealably mounted to said mounting end of said first male connector so that blood received by said first male connector will be delivered to said tubing, said tubing being flexible and substantially clear so that blood received thereby will be visible to the medical personnel;
  a coupling including an elongate hollow shaft and a connector member attached to a first end of said shaft for fixedly and sealably coupling said second end of said tubing to said coupling thereby to allow blood received by said tubing to be delivered to said coupling, said coupling further including an adapter sleeve attached to a second end of said shaft for interfacing said shaft with blood storage devices, said coupling also including a second female connector fixedly attached to said shaft intermediate said adapter sleeve and said connector member and in flow communication with said connector member so that blood received by said coupling is in flow communication with said second female connector; and a plug positioned within said shaft of said coupling intermediate said second female connector and said adapter sleeve, said plug being adapted to allow gases to escape from said shaft and to effectively block the flow of blood from said shaft to said adapter sleeve.

22. The blood sampling device as recited in claim 21, further comprising a second needle member having an insertion end, a coupling end and a coaxial channel extending from said insertion end to said coupling end; and vacutainer means for storing blood withdrawn from the patient, said vacutainer means being fixedly attached to said second needle member, said adapter sleeve being configured so that said vacutainer means may be press fit into said adapter sleeve and so that said second needle member may be inserted through said plug thereby to transport blood received by said shaft of said coupling to said vacutainer means.

23. The blood sampling device as recited in claim 22, further comprising a needle guide positioned interior of said coupling intermediate said plug and said adapter sleeve for guiding said second needle member so that said second needle member is inserted into said plug coaxial with said coupling.

24. The blood sampling device as recited in claim 21, further comprising a needle guide positioned interior of said coupling intermediate said plug and said adapter sleeve for guiding a needle associated with a blood storage device so that the needle is inserted coaxially into said coupling.

25. The blood sampling device as recited in claim 21, further comprising capping means adapted to mate with said second female connector thereby to seal said second female connector to prevent the escape of blood from said second female connector.

26. The blood sampling device as recited in claim 21, further comprising a syringe for temporarily storing blood, said syringe including a blood storage chamber and a plunger positioned within said blood storage chamber, said syringe further including a second male connector in flow communication with said blood storage chamber and adapted to mate with said second female connector so that blood received by said coupling may be stored within said syringe.

27. The blood sampling device as recited in claim 26, further comprising a needle guide positioned interior of said coupling intermediate said plug and said adapter sleeve for guiding a needle associated with a blood storage device so that the needle is inserted coaxially into said coupling.

28. The blood sampling device as recited in claim 27, further comprising a second needle member having an insertion end, a coupling end and a coaxial channel extending from said insertion end to said coupling end;

vacutainer means for storing blood withdrawn from the patient, said vacutainer means being fixedly attached to said second needle member, said adapter sleeve being configured so that said vacutainer means may be press fit into said adapter sleeve and so that said second needle member may be inserted through said plug thereby to transport blood received by said shaft of said coupling to said vacutainer means.

29. The blood sampling device as recited in claim 27, further comprising first, second and third capping devices for sealing said first needle member, said second female connector and said adapter sleeve, respectively.

30. The blood sampling device as recited in claim 21, further comprising valve means coupled to said second female connector for selectively allowing fluid communication between said second female connector and said shaft.

31. A blood sampling device for use by medical personnel to withdraw and store a blood sample from a patient comprising:

needle means for withdrawing blood from the patient;

syringe means for temporarily storing a first portion of blood withdrawn from the patient;

adaptor means for receiving a blood storage device and being adapted to conduct blood thereto for storage; and coupling means for sealably coupling said needle means to said adaptor means and to said syringe means, said syringe means being intermediate to said needle means and said adaptor means, said coupling means including flow control means positioned adjacent said adaptor means between said adaptor means and said syringe means for venting air trapped within said needle means and said coupling means, said syringe means and said coupling means being further adapted to return the first portion of blood to the patient.

32. The blood sampling device as recited in claim 31 wherein said coupling means comprises a coupling including an elongate hollow shaft and a connector member attached to a first end of said shaft for fixedly coupling said needle means to said coupling, said adapter means being attached to a second end of said shaft, said coupling also including a connector member fixedly attached to said shaft intermediate said adapter means and said connector member for receiving said syringe means.

33. The blood sampling device as recited in claim 32 wherein said flow control means comprises a plug positioned within said shaft of said coupling intermediate said connector member and said adapter means.

34. The blood sampling device as recited in claim 33 wherein said plug comprises a microporous hydrophobic plug.

35. The blood sampling device as recited in claim 33 wherein said needle means includes a needle for insertion into the patient to withdraw the blood sample and an elongate tubing for conducting blood withdrawn from the patient to said coupling, said tubing being flexible and being substantially clear so that blood conducted thereby is visible to the medical personnel.

* * * * *